United States Patent
Young et al.

(10) Patent No.: US 8,511,313 B2
(45) Date of Patent: Aug. 20, 2013

(54) VAGINAL SHIELD

(76) Inventors: Wendy Ann Young, Lake Tapps, WA (US); Lisa Nanette Alexander, East Orting, WA (US)

( * ) Notice: Subject to any disclaimer, the term of this patent is extended or adjusted under 35 U.S.C. 154(b) by 1011 days.

(21) Appl. No.: 12/252,676

(22) Filed: Oct. 16, 2008

(65) Prior Publication Data

US 2009/0101155 A1   Apr. 23, 2009

Related U.S. Application Data

(60) Provisional application No. 60/999,520, filed on Oct. 19, 2007, provisional application No. 61/079,754, filed on Jul. 10, 2008.

(51) Int. Cl.
*A61F 6/06*   (2006.01)
*A61F 6/14*   (2006.01)
*A61F 5/37*   (2006.01)
*A61C 5/14*   (2006.01)

(52) U.S. Cl.
USPC ............ 128/830; 128/841; 128/846; 128/859

(58) Field of Classification Search
USPC ..... 128/830, 846, 859, 841, 891; 600/38–41, 600/29; 601/84
See application file for complete search history.

(56) References Cited

U.S. PATENT DOCUMENTS

| | | | |
|---|---|---|---|
| 2,534,934 A | 12/1950 | Viniegra | |
| 4,043,329 A | 8/1977 | DiMatteo | |
| 4,421,511 A | 12/1983 | Steer et al. | |
| 4,496,355 A | 1/1985 | Hall et al. | |
| 4,795,449 A | 1/1989 | Schneider et al. | |
| 4,822,347 A | 4/1989 | MacDougall | |
| 4,846,819 A | 7/1989 | Welch | |
| 4,938,233 A | 7/1990 | Orrison | |
| 5,207,233 A | 5/1993 | Barnes | |
| 5,269,320 A | 12/1993 | Hunnicutt | |
| 5,669,395 A | 9/1997 | Thompson | |
| D396,284 S | 7/1998 | Schaefer | |
| 5,895,349 A * | 4/1999 | Tihon | 600/29 |
| D444,561 S | 7/2001 | Stein | |
| D455,488 S | 4/2002 | James | |
| D482,446 S | 11/2003 | Rainville-Lonn et al. | |
| 6,681,771 B2 | 1/2004 | Durette | |
| 6,732,737 B1 | 5/2004 | Brown | |
| 6,733,438 B1 | 5/2004 | Dann et al. | |
| 7,171,699 B2 | 2/2007 | Ernest et al. | |
| 2009/0036858 A1 * | 2/2009 | Van Den Bogart et al. | 604/385.03 |
| 2009/0065008 A1 * | 3/2009 | Clodius-Talmadge | 128/830 |

* cited by examiner

*Primary Examiner* — Patricia Bianco
*Assistant Examiner* — Ophelia A Hawthorne
(74) *Attorney, Agent, or Firm* — R. Reams Goodloe, Jr.

(57) ABSTRACT

A protective shield. The protective shield is provided in a generally cupped structure sized to accommodate and shaped with sufficient volume to receive therein adult human female genitalia. The protective vaginal shield includes a soft, flexible outer lip that is generally configured in the shape of an arcuate section made through an ovoid shape substantially along the longitudinal axis thereof. Extending inwardly and downwardly from the outer lip are outer sloping sidewalls. A longitudinally extending nose portion is provided. Inner sloping sidewalls extend from the outer sloping sidewalls to the longitudinally running nose portion. In one embodiment, the inner sloping sidewalls comprise a pair of opposing concave shaped structures, to provide a secure handle grip. In an embodiment, the protective shield may be provided in a disposable material.

26 Claims, 3 Drawing Sheets

VAGINAL SHIELD

RELATED PATENT APPLICATIONS

This application claims priority from prior U.S. Provisional Patent Application Ser. No. 60/999,520, filed on Oct. 19, 2007, and from prior U.S. Provisional Patent Application Ser. No. 61/079,754, filed on Jul. 10, 2008, the disclosures of which, including the specification, drawing, and claims, are incorporated herein in its entirety by this reference.

COPYRIGHT NOTICE

A portion of the disclosure of this patent document contains material that is subject to copyright protection. The patent owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to protective devices, and more particularly, to protective devices for the female groin region.

BACKGROUND

Although various devices for the protection of the female groin region have been provided in the prior art, such prior art devices known to us have been directed to either the needs of artists, models, dancers and the like, who are looking for a shield for female genitalia during performances, or to medical devices, such as may be used by patients undergoing some type of medical procedure. However, available versions of protective shields of which we are aware are not configured for use in an easily placed, strapless manner adaptable for use by sun bathers, nor have they been provided in inexpensive materials that are easily and inexpensively replaceable, i.e., having a disposable configuration. Depending on the situation, the needs of sunbathers, or users of indoor tanning beds, or of actors in adult films, for example and not by way of limitation, have not been adequately addressed by prior art devices of which we are aware. Thus, there remains a significant and as yet unmet need for a simple, anatomically compatible disposable shield which can be easily and quickly installed for use in the protection of female genitalia, especially with respect to protection against ultraviolet exposures, so as to provide protection against sunburn of sensitive body parts.

SUMMARY

We have now developed a firm yet flexible disposal shield having sufficient volume and anatomically sized and shaped to receive and enclose adult female genitals. In particular, the shield, which may in an embodiment be disposable, is designed, shaped, and sized for use by a woman to protect the vaginal area, and in particular, the inner vulva area. In order to effectively provide such protection, the shield has been designed to snugly fit into place and closely adhere to the natural shape and form of such portions of a woman's body.

In an embodiment, a shield may be provided as a generally canoe shaped guard with a handle on the canoe bottom. In an embodiment, a disposable shield may be provided as a generally concave cupped structure, with an engaging lip shaped as the outer edge of an arcuate section (i.e., slightly varying height H dimension) cut generally longitudinally through an ovoid, or egg like shaped structure. Extending inward and downward from the outer engaging lip are outer side sloping sidewalls. A longitudinally running handle portion is provided, sized and shaped for manual manipulation during installation. Inner sloping sidewalls extend from the outer sloping sidewalls to the longitudinally running handle portion. In an embodiment, the inner sloping sidewalls may be provided as a pair of opposing concave shaped structures.

In an embodiment, the shields taught herein may be configured for manufacture in inexpensive, disposable materials. In an embodiment, the disposable shields taught herein may be provided in recyclable disposable materials, such as recyclable plastics, for example polyethylene. In an embodiment, the disposable shields may be provided with a UV shielding material as part of the material of construction. In an embodiment, the disposable shields taught herein may be provided in a hypo-allergenic material of construction. In an embodiment, such disposable shields can be provided in a flexible material.

The shield described and shown herein may be useful for, and used in many circumstances, such as when using depilatory creams, or waxes, or while using electric shavers, electrolysis, razors, or scissors, i.e., generally during hair removal from the pubic area in this regard, such disposable shields may be useful for protection during medical procedure preparation activities. Similarly, such disposable shields may be useful when applying hair coloring. Such shields may be useful when trying on swim suits or other intimate apparel. And, such disposable shields may be especially useful when tanning outdoors under the sun, or when using indoor tanning beds, or even when using tanning spray or medicaments.

The foregoing briefly describes an exemplary shield for use in protection of a woman's inner vulva area, which shield may, in an embodiment, be provided as a disposable shield. The various objectives, features and advantages of the invention(s) will be more readily understood upon consideration of a detailed description, taken in conjunction with careful examination of the accompanying figures of the drawing.

BRIEF DESCRIPTION OF DRAWING

In order to enable the reader to attain a more complete appreciation of the invention, and of the novel features and advantages thereof, attention is directed to the following detailed description when considered in connection with the accompanying drawings, wherein.

Figure 1:
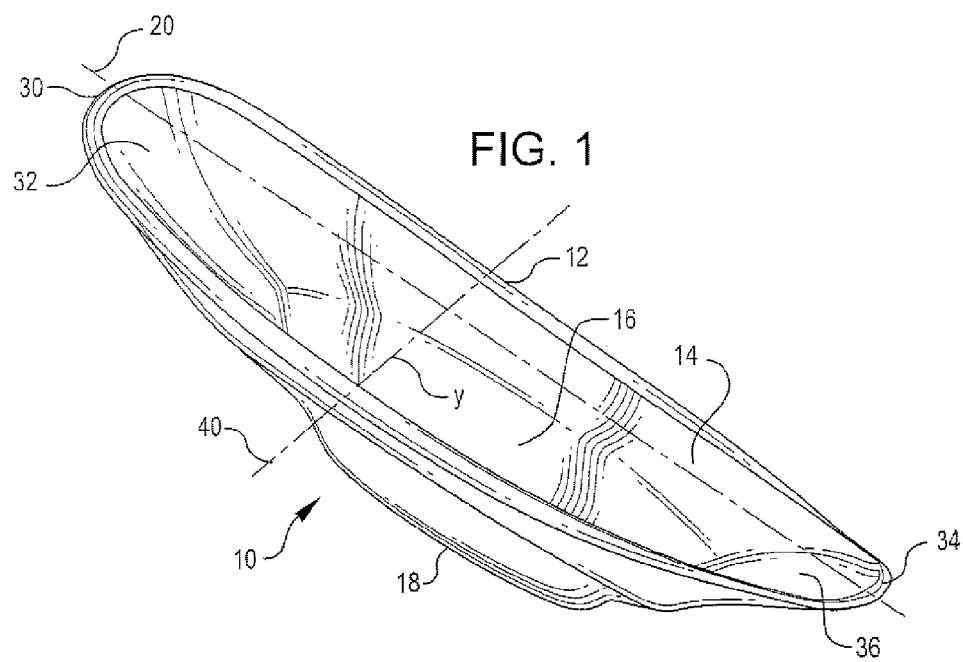
FIG. 1 provides a perspective view of an embodiment for a vaginal shield, showing the overall shape, including outer rim, sloping sidewalls, and sloping inner wall having outer portions, and a handle.

In the various figures of the drawing, like features may be illustrated with the same reference numerals, without further mention thereof. Further, the foregoing figures are merely exemplary, and may contain various elements that might be present or omitted from actual implementations of various embodiments depending upon the circumstances. An attempt has been made to draw the figures in a way that illustrates at least those elements that are significant for an understanding of the various embodiments and aspects of the invention.

However, various other elements of a vaginal shield, especially as applied for different variations of the materials of construction, as well as different embodiments of artistic elements such as the precise shape of components or visual design of various elements, may be utilized in order to provide a useful, reliable, and economical protective vaginal shield, particularly for the inner vulva area.

DETAILED DESCRIPTION

Attention is directed to the various drawings, as described herein above, where features of an exemplary vaginal shield are shown. First, see FIG. 1, which provides a perspective view of an embodiment for a vaginal shield 10, showing the overall shape, including outer rim or lip 12, outer sloping sidewalls 14, and inner sloping sidewalls 16, and a handle 18. In an embodiment, the handle 18 may be oriented substantially along the longitudinal axis 20 of the vaginal shield 10. More generally, as seen in FIG. 1, the shield 10 is provided as a generally cupped structure sized to accommodate and shaped with sufficient volume to receive therein adult human female genitalia, and more particularly, primarily the inner labia, clitoris, and vaginal opening.

The outer lip 12 of the vaginal shield 10 may in an embodiment be generally configured in the shape of an arcuate section (i.e., slightly varying in offset transversely) made through an ovoid shape substantially along the longitudinal axis thereof, such as along longitudinal axis 20 of shield 10. In an embodiment, the outer lip 12 may be provided in the form of a resilient, flexible material composition. The outer sloping sidewalls 14 extend generally inwardly and downwardly from the outer lip 12. The handle 18 may, in an embodiment, be provided in a configuration that extends along the longitudinal axis 20 of the disposable shield 10. In an embodiment, the inner sloping sidewalls 16 extend from the outer sloping sidewalls 14 to the handle portion 18.

The shield 10 may, in an embodiment, be provided manufactured in a plastic material composition. Various such plastic compositions are suitable for manufacturing the vaginal shield 10 by a molding process. For example, the vaginal shield 10 may be provided in a molded plastic material that includes polyethylene as a primary component of the material composition. One suitable polyethylene composition for disposable shield 10 is low density polyethylene. Further, the disposable shield 10 may include, either as a primary constituent or as an additive, an ultraviolet attenuator material, wherein the ultraviolet attenuator is sufficiently effective to substantially block ultraviolet radiation transmission through said shield, whether the source of such ultraviolet ("UV") radiation is the sun or lights used in an indoor tanning salon. In an embodiment, the vaginal shield 10 is made from a soft, flexible material. In an embodiment, the vaginal shield 10 may be made from a hypo-allergenic material. In an embodiment, the vaginal shield 10 may be made from a disposable material, such as a selected plastic composition.

Figure 3:
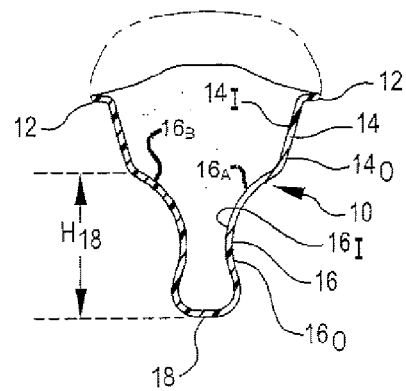
FIG. 3 is a vertical cross section of an embodiment for a vaginal shield, taken along line 3-3 of FIG. 2, showing how the device may be provided with inner sidewalls having a generally concave shape to assist in formation of a handle, for ease in manual gripping during installation.

As better seen in FIG. 3, the inner sloping sidewalls 16 may, in an embodiment, be provided as a pair of opposing concave shaped structures $16_A$ and $16_B$. In an embodiment, a smooth inner surface portion $14_I$ is provided for the outer sloping sidewalls 14. In an embodiment, a smooth inner surface portion $16_I$ is provided for the inner sloping sidewalls 16. In an embodiment, a smooth outer surface portion $14_O$ is provided for outer sloping sidewalls 14. In an embodiment, a smooth outer surface portion $16_O$ is provided for inner sloping sidewalls 16.

Figure 2:
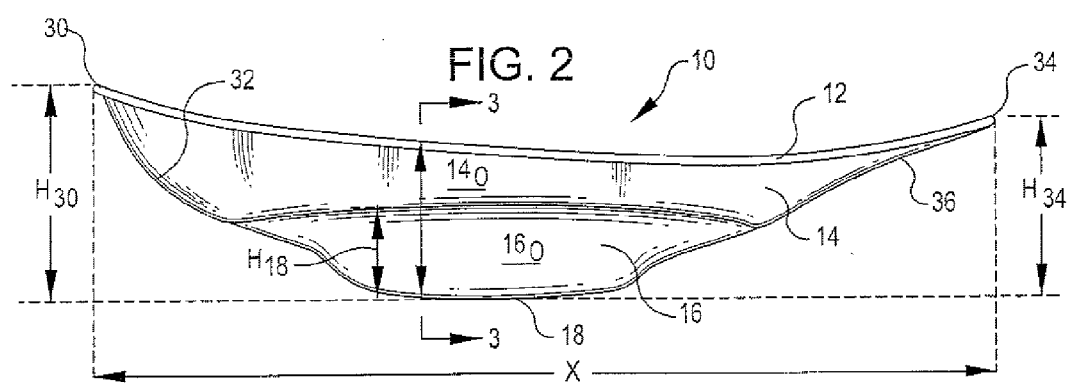
FIG. 2 is side view of an embodiment for a vaginal shield, showing the outer rim, the sloping outer sidewall, the inner sidewall and handle portion, as well as illustrating the curvature of the outer lip.
Figure 7:
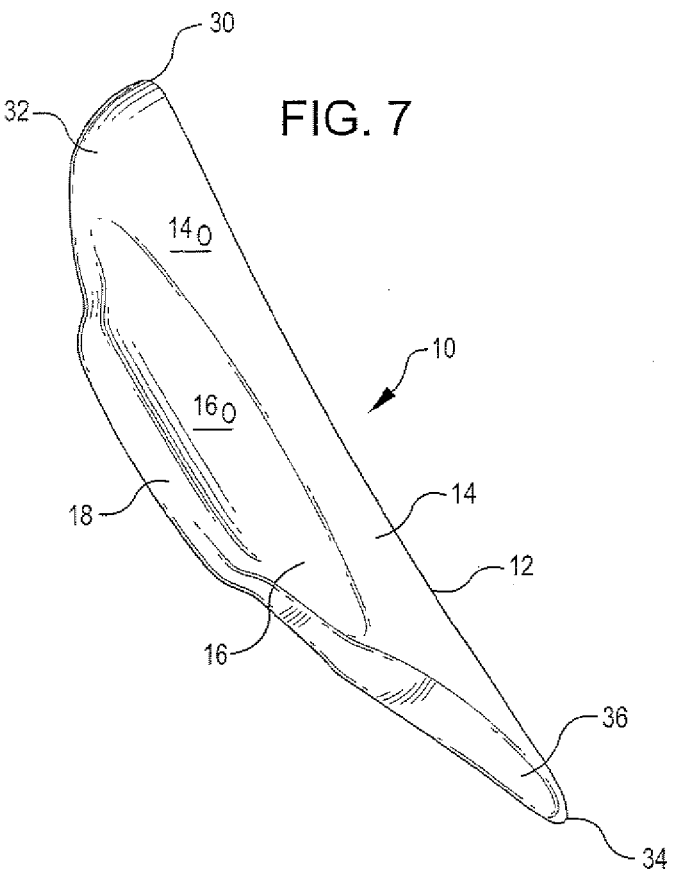
FIG. 7 is a perspective view of an embodiment for a vaginal shield, showing in detail the handle that is sized and shaped for gripping between a user's thumb and forefinger during installation.

As shown in FIGS. 2 and 7, for example, in an embodiment, a vaginal shield 10 may be provided in a configuration where an upper or first end 30 has a generally nose shaped portion 32. Also, in an embodiment, a shield 10 may be provided in a configuration where a lower or second end 34 has a generally flat sloping tail shaped portion 36. The height H dimensions for various components of vaginal shield 10 are shown in FIG. 2. At first end 30, a height $H_{30}$ is illustrated, that is comparable to, or slightly more than, width Y. At second end 34, a height $H_{34}$ is illustrated. The height $H_{18}$ of handle 18 is also shown in FIG. 3.

As shown in FIGS. 1 and 2, for example, in an embodiment, a vaginal shield 10 may be sized, along longitudinal axis 20, in a length X of from about three (3) to about four (4) inches long. In an embodiment, a vaginal shield 10 may be sized, along a transverse axis 40, in a width Y of from about three quarters of an inch (0.75 inches) to about one inch (1.0 inches).

Figure 4:
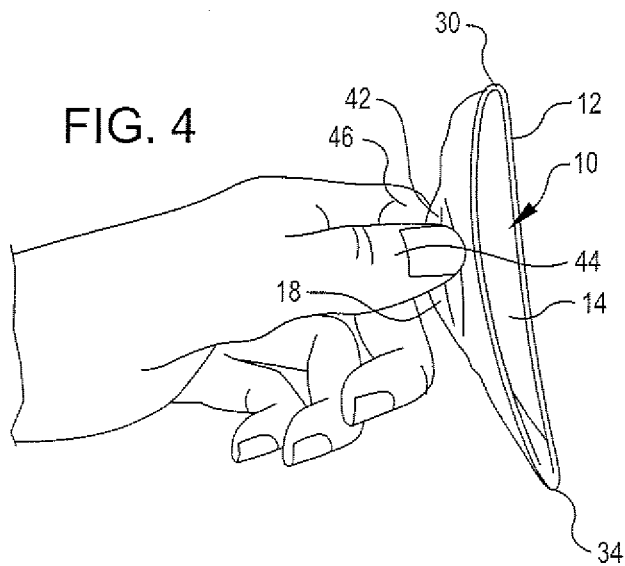
FIG. 4 is a perspective view of an embodiment for a vaginal shield, showing how the device may be gripped at the handle, between a user's thumb and forefinger, for manual installation.
Figure 5:
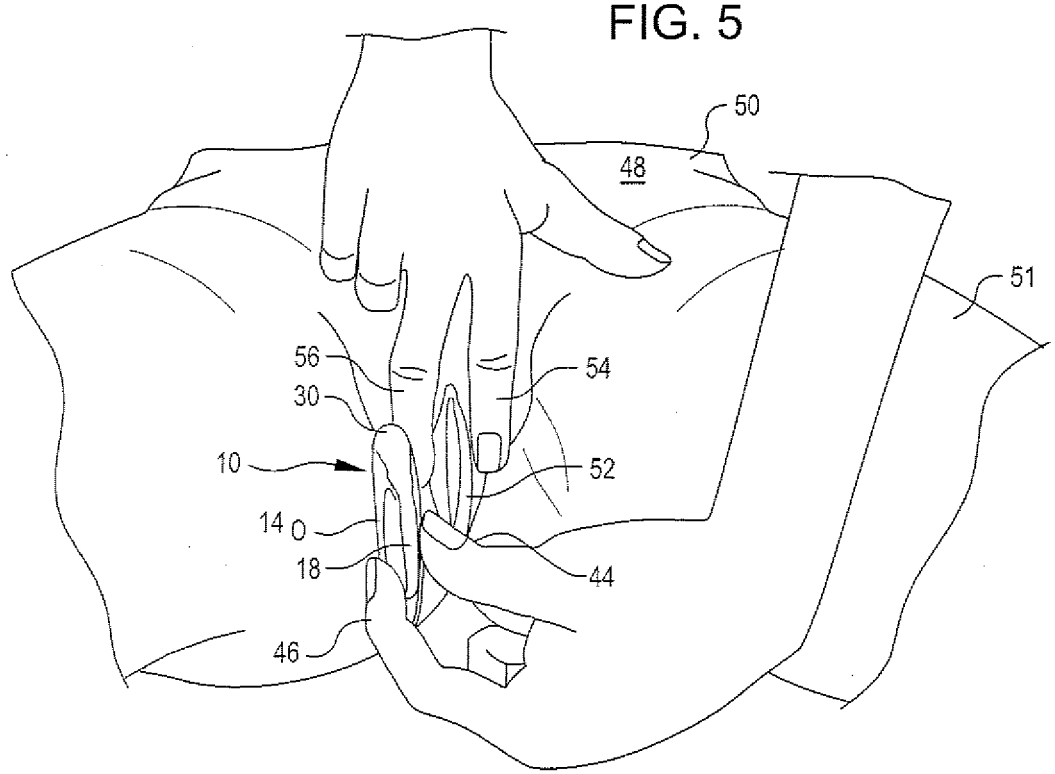
FIG. 5 is a perspective view of an embodiment for a vaginal shield being installed, with the shield being gripped at the handle, between a user's thumb and forefinger, during manual installation.
Figure 6:
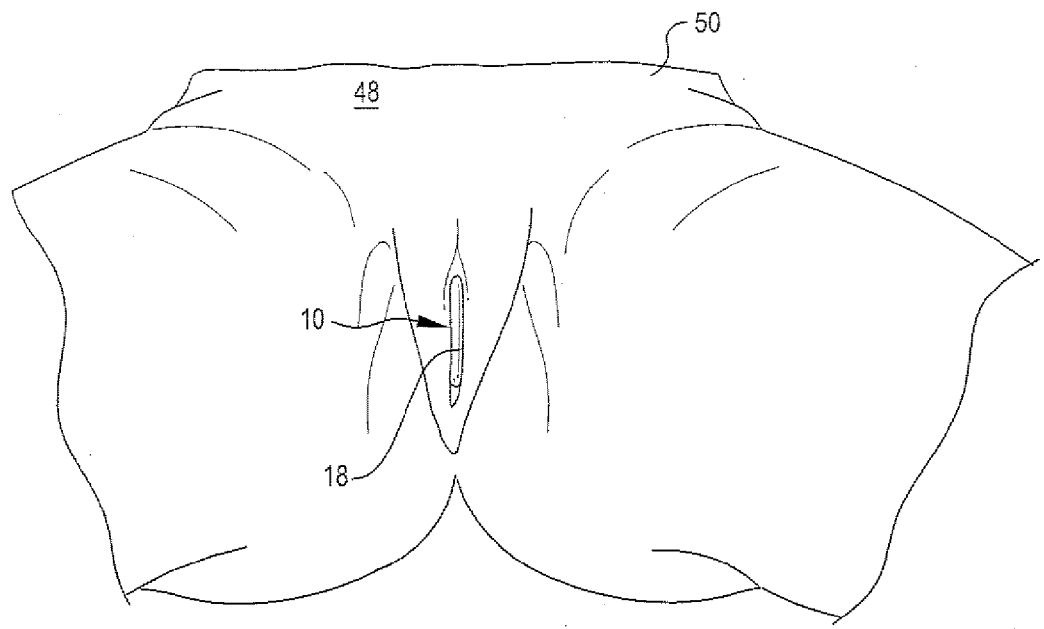
FIG. 6 is a perspective view of an embodiment for a disposable shield, showing the shield in place for use, after installation.

As depicted in FIG. 4, a vaginal shield 10 may include a handle 18 that has ribs 42. As seen in FIGS. 4 and 5, the handle 18 (also illustrated in FIG. 3 above) may be grasped between the thumb 44 and forefinger 46 of a user. FIGS. 4, 5, and 6 illustrate how to use the disposable shield 10. In particular, the disposable shield is grasped between the thumb 44 and forefinger 46. The tail portion 36 is oriented downward, and the nose portion 32, having a wider, deeper cup configuration, is oriented upward toward the front 48 of user 50. To install the disposable shield, user 50 can raise one leg 51 or squat slightly and spread the outer labia 52 as noted in FIG. 5 with fingers 54 and 56. The shield 10 is gently placed over the inner labia/clitoris and vaginal opening, and the outer labia is folded over the smooth outer surface portion $14_O$ of outer sloping sidewalls 14 and/or the smooth outer surface portion $16_O$ of inner sloping sidewalls 16. When properly positioned as illustrated in FIG. 6, the vaginal shield 10 is comfortable for user 50.

The vaginal shield 10 should feel secure prior to application of depilatory creams, waxes, or lotions. In order to create a more powerful seal, a personal lubricant may be spread around the smooth inner surface portion $14_I$ of the outer sloping sidewalls 14, and/or the smooth inner surface portion $16_I$ of the inner sloping sidewalls 16. Before removal of the vaginal shield 10, all creams, lotions, and waxes, etc., should be completely removed.

It is to be appreciated that the various aspects, features, structures, and embodiments of a vaginal shield as described herein is a significant improvement in the state of the art. The shield design provided is simple, reliable, inexpensive, and easy to use. In an embodiment, an inexpensive, disposable vaginal shield is provided. Although only a few exemplary aspects and embodiments have been described in detail, various details are sufficiently set forth in the drawing figures and in the specification provided herein to enable one of ordinary skill in the art to make and use the invention(s), which need not be further described by additional writing.

Importantly, the aspects, features, structures, and embodiments described and claimed herein may be modified from those shown without materially departing from the novel teachings and advantages provided, and may be embodied in other specific forms without departing from the spirit or essential characteristics thereof. Therefore, the various aspects and embodiments presented herein are to be considered in all respects as illustrative and not restrictive. As such, this disclosure is intended to cover the structures described herein and not only structural equivalents thereof, but also equivalent structures. Numerous modifications and variations are possible in light of the above teachings. The scope of the invention, as described herein is thus intended to include variations from the various aspects and embodiments provided which are nevertheless described by the broad meaning and range properly afforded to the language herein, as explained by and in light of the terms included herein, or the legal equivalents thereof.

The invention claimed is:

1. A disposable shield, comprising:
a generally cupped structure sized to accommodate and shaped with sufficient volume to receive therein adult human female genitalia, comprising
an outer lip, said outer lip generally configured in the shape of an arcuate section made through an ovoid shape substantially along the longitudinal axis thereof;
outer sloping sidewalls, said outer sloping sidewalls extending generally inwardly and downwardly from said outer lip;
a longitudinally extending handle portion;
inner sloping sidewalls, said inner sloping sidewalls extending from said outer sloping sidewalls to said longitudinally running handle portion.

2. The disposable shield as set forth in claim 1, wherein said shield comprises a molded plastic material.

3. The disposable shield as set forth in claim 2, wherein said molded plastic material comprises polyethylene.

4. The disposable shield as set forth in claim 3, wherein said polyethylene comprises low density polyethylene.

5. The disposable shield as set forth in claim 2, wherein said disposable shield comprises an ultraviolet attenuator, said ultraviolet attenuator sufficient to substantially block ultraviolet radiation transmission through said shield.

6. The disposable shield as set forth in claim 1, wherein said disposable shield comprises a soft, flexible material.

7. The disposable shield as set forth in claim 6, wherein said disposable shield comprises a hypo-allergenic material.

8. The disposable shield as set forth in claim 1, wherein said inner sloping sidewalls comprise a pair of opposing concave shaped structures.

9. The disposable shield as set forth in claim 1, wherein said outer lip comprises a resilient, flexible rim portion.

10. The disposable shield as set forth in claim 1, wherein said disposable shield comprises a smooth inner surface portion.

11. The disposable shield as set forth in claim 1, wherein said disposable shield comprises a smooth outer surface portion.

12. The disposable shield as set forth in claim 1, wherein said disposable shield comprises a first end having a generally nose shaped portion.

13. The disposable shield as set forth in claim 1, wherein said disposable shield comprises a second end having a generally flat sloping tail shaped portion.

14. The disposable shield as set forth in claim 1, wherein said disposable shield is sized, along a longitudinal axis, of from about three (3) to about four (4) inches long.

15. The disposable shield as set forth in claim 1, wherein said disposable shield is sized, along a transverse axis, of from about three quarters of an inch (0.75 inches) to about one inch (1.0 inches).

16. The disposable shield as set forth in claim 1, wherein said handle comprises a ribbed handle.

17. A protective shield, comprising:
a generally cupped structure sized to accommodate and shaped with sufficient volume to receive therein adult human female genitalia, comprising
an outer lip, said outer lip generally configured in the shape of an arcuate section made through an ovoid shape substantially along the longitudinal axis thereof;
outer sidewalls, said outer sidewalls extending generally inwardly and downwardly from said outer lip;
a handle portion;
inner sidewalls, said inner sidewalls extending from said outer sidewalls to said handle portion.

18. The shield as set forth in claim 17, wherein said shield comprises a molded plastic material.

19. The shield as set forth in claim 18, wherein said disposable shield comprises an ultraviolet attenuator, said ultraviolet attenuator sufficient to substantially block ultraviolet radiation transmission through said shield.

20. The shield as set forth in claim 17, wherein said inner sidewalls comprise a pair of opposing concave shaped structures.

21. The shield as set forth in claim 17, wherein said outer lip comprises a resilient, flexible rim portion.

22. The shield as set forth in claim 17, wherein said disposable shield comprises a first end having a generally nose shaped portion.

23. The shield as set forth in claim 17, wherein said disposable shield comprises a second end having a generally flat sloping tail shaped portion.

24. The shield as set forth in claim 17, wherein said disposable shield is sized, along a longitudinal axis, of from about three (3) to about four (4) inches long.

25. The shield as set forth in claim 17, wherein said disposable shield is sized, along a transverse axis, of from about three quarters of an inch (0.75 inches) to about one inch (1.0 inches).

26. The shield as set forth in any one of claims 17 through 25, wherein said shield comprises a disposable shield.

* * * * *